United States Patent [19]
Saffert et al.

[11] Patent Number: 4,959,552
[45] Date of Patent: Sep. 25, 1990

[54] MICROSCOPE ARRANGED FOR MEASURING MICROSCOPIC STRUCTURES

[75] Inventors: Ralf Saffert, Lauterstein; Albert Schilling, Aalen, both of Fed. Rep. of Germany

[73] Assignee: Carl-Zeiss-Stiftung, Heidenheim/Brenz, Fed. Rep. of Germany

[21] Appl. No.: 303,923

[22] Filed: Jan. 30, 1989

[30] Foreign Application Priority Data

Feb. 9, 1988 [DE] Fed. Rep. of Germany ....... 3803854

[51] Int. Cl.$^5$ ............................................. G01N 21/86
[52] U.S. Cl. ................................................ 250/560
[58] Field of Search ............... 250/216, 231 SE, 548, 250/560, 231.14, 231.13, 231.18, 201.3, 201 AF; 350/502, 507, 6.2, 521; 356/400

[56] References Cited

U.S. PATENT DOCUMENTS

| | | | |
|---|---|---|---|
| 3,941,980 | 3/1976 | Okamoto et al. | 377/3 |
| 4,293,218 | 10/1981 | Nielson et al. | 350/6.2 |
| 4,373,817 | 2/1983 | Coates | 356/384 |
| 4,600,832 | 7/1986 | Grund | 250/201 |
| 4,606,616 | 8/1986 | Parker | 350/521 |
| 4,685,775 | 8/1987 | Goodman et al. | 350/486 |

FOREIGN PATENT DOCUMENTS

| | | |
|---|---|---|
| 1070586 | 6/1967 | United Kingdom . |
| 1301626 | 1/1973 | United Kingdom . |
| 1347777 | 2/1974 | United Kingdom . |
| 1400253 | 7/1975 | United Kingdom . |

Primary Examiner—David C. Nelms
Assistant Examiner—George Beck
Attorney, Agent, or Firm—Stonebraker, Shepard & Stephens

[57] ABSTRACT

A microscope (1) arranged for measuring microscopic structures uses punctiform bundles of rays from a point source (31, 34) of light focused by an optical system on a structure to be measured so that a photoelectric detector (15) can receive the ray bundles reflected from the structure. Plane plates (30a, 30b) arranged in a non-parallel ray portion of the path of the optical system can be pivoted through predetermined angles for moving the focal point of the ray bundles on the structure. Encoders (61a, 61b) are coupled with the plates and arranged for measuring the pivot angles used in moving the focal point; and a processor (20) supplied with signals from the encoders and from the detector (15) is arranged for calculating the linear dimensions of the structure over which the focal point has moved.

8 Claims, 4 Drawing Sheets

MICROSCOPE ARRANGED FOR MEASURING MICROSCOPIC STRUCTURES

BACKGROUND

Devices for measuring microscopic structures are used predominantly in the microelectronic industry for inspecting wafers or masks. Such devices are frequently referred to as "line-width measuring instruments".

The known devices for this purpose are constructed in the manner of a microscope. In other words, the actual measuring instrument is developed either as an accessory to a microscope or as an adaptation of an existing microscope that has been modified for measuring purposes. The known instruments, however, differ in their principle of measurement and can be classified on that basis into three categories.

For a first category, some instruments can post enlarge and focus an optical intermediate image of the microscope onto a tube of a television camera. The actual measurement (of the width of a portion of the structure being imaged, for example) is then accomplished electronically by evaluating the video signal of the television camera. These instruments suffer the disadvantage of being limited to the resolving power of the video camera, so that they are not suitable for highly precise measurements in the submicron range.

The second category includes instruments having a slit diaphragm viewed by a photomultiplier and moved along an intermediate image of the microscope. Examples of instruments operating this way are described in U.S. Pat. No. 4,373,817, issued Feb. 15, 1983, by Coates, and U.S. Pat. No. 4,600,832, issued July 15, 1986, by Grund. Especially high resolution cannot be attained with these instruments either, because it is not practically possible to guide the slit diaphragm precisely and to determine its position accurately, as an element of the measuring process. Furthermore, the scanning speed of this type of instrument is relatively slow.

The second category can also include instruments that displace the object itself in a plane perpendicular to the optical axis, rather than moving a slit diaphragm in the intermediate image of the microscope. The object can be moved for measurement purposes, by means of piezotranslators. This is even more expensive, however, since movement of the object must be effected and measured with a precision that is higher by the linear magnification of the microscope objective—about 40× or 100×. This puts submicron accuracy out of reach.

The third category includes instruments that do not measure in the object image plane, but move a beam of light focused in a punctiform manner over the structure to be measured. Such instruments are described, for example, in European Patent Application No. EP 0 168 643 A2, published Jan. 22, 1986, by Bille et al., and Federal Republic of Germany Offenlegungsschrift No. DE 36 10530 A1, published Oct. 2, 1986, by Horikawa.

The instruments of these patents employ swivel mirrors or "galvanometer scanners" for deflecting or moving the measuring spot over a structure to be measured. This can produce high measurement speeds, and the measuring spot can be moved rapidly over a relatively large region of a specimen. But for accurate, submicron measurement purposes, speed and range of movement of the measurement spot constitutes a disadvantage, because relatively large movements of the measurement spot are brought about by relatively small changes in angles of deflection of the swivel mirrors. Since the actual measurement is derived from the deflection angles of the mirrors, the tiny deflection angles involved in moving the spot over structures of submicron width limits the resolution of these instruments. Furthermore, galvanoscanners are subject to hysteresis effects that limit the accuracy of their angular measurements. Together, these effects make such instruments unacceptable for submicron measurement.

As explained more fully below, our measuring microscope uses a pivoting plane plate that moves a measuring spot. A plane plate that pivots has been suggested by U.S. Pat. No. 3,941,980, issued Mar. 2, 1976, by Okamoto et al., for adjusting wafers relative to a mask used for their exposure—a purpose quite different from ours. The device of the U.S. Pat. No. 3,941,980 patent is called a "scanning photoelectric microscope"; and its rectangular, plane-parallel prism is pivoted with a uniform speed to move the adjustment marks of the wafer or the mask, as these marks are focused on slit diaphragms in the intermediate image. The signals of detectors arranged behind the measurement diaphragms serve to adjust the wafer precisely with respect to the mask.

For measurement purposes, the device of U.S. Pat. No. 3,941,980 operates like the instruments mentioned in the second category—on the basis of moving the entire object image relative to a measurement diaphragm. Moreover, the pivoting plate serves only for adjusting the wafer position and is not involved in measuring any structure on the wafer itself. Furthermore, like the devices mentioned in categories 1 and 2, this device has the disadvantage that the entire object is illuminated, which reduces the sensitivity of the light detection system and thereby reduces the precision of any obtainable measurement.

U.S. Pat. No. 4,685,775, issued Aug. 11, 1987, by Goodman et al., also suggested a pivoting plane plate cooperating with beam-deflecting pivot mirrors in a laser-scanning microscope, for displacing the laser beam perpendicular to the optical axis. The plane plate in this instrument, however, serves merely to compensate for the travel of the beam off the axis of the pupil of the microscope objective, as caused by the first pivot mirror, since the beam cannot be held precisely at the locus of the pupil. The actual deflecting or moving of the focused laser beam over the structure being measured is accomplished solely by the pivot mirror. Also, no device is included in this microscope for measuring line width, so that the problem we have solved is not addressed by this instrument.

The aim of our invention is to arrange a microscope for measuring microscopic structures with high precision and reliability in the submicron range. We also aim at keeping the measurement device as inexpensive and compact as possible, so that it can serve as an affordable accessory to a microscope.

SUMMARY OF THE INVENTION

To accomplish submicron structure measurement with a microscope, we use punctiform bundles of rays from a point source of light focused by an optical system on the structure to be measured so that a photoelectric detector can receive the ray bundles reflected from the structure. For moving the focal point of the ray bundles over the structure to be measured, we use a plane plate arranged in a non-parallel ray portion of the path of the optical system so that the plate can be pivoted through a predetermined angle. An encoder coupled with the plate is arranged for measuring the pivot angle of the plate used in moving the focal point over the structure being measured; and a processor is supplied with signals from the encoder and from the detector, so that the processor can calculate the linear dimensions of the structure over which the focal point has moved. We also prefer that two plane plates be pivoted on axes perpendicular to each other and that encoders for the pivot angles of both plates transmit signals to the processor in an evaluation unit.

The pivot angle of a plane plate in the convergent ray path of the optical system can represent the result of the measurement made by moving the focal point over a structure. The obtainable movement of the measurement spot depends on the thickness of the plane plate, and the conversion from the pivot angle to the spot displacement can be determined by plate thickness. This allows even submicron deflections of the measurement spot to be accurately measured without additional expense solely by means of an angle encoder placed on the axis of rotation of the plane plate. The demands on measurement of the pivot angle, when using a plane plate with a thickness of one or two millimeters, are about two orders of magnitude less than measurement by the angle of a pivot mirror for deflecting a beam, as suggested for the devices in category 3. Although a plane plate can move the measurement spot only by slight amounts within the viewing field of the microscope objective, this does not impair the measurement of tiny structures having widths in the submicron range.

The point source of light for the measurement spot is preferably ultraviolet radiation, and the optical systems in the measurement ray path and in the objective and tube lens portion of the microscope used for focusing the measurement spot are made of materials suitable for transmitting ultraviolet radiation. Since the size of the measurement spot depends on the wave length of the measurement light, the measurement spot can be kept small by using ultraviolet radiation. We also prefer that a point diaphragm be arranged in front of the point source and the detector, specifically in a plane conjugate to the point source of measurement light. The resulting confocal construction allows only light coming from within the depth-of-focus range to contribute to the measurement of the line width, and contrast-reducing portions of light from planes that are out of focus are masked out by the resulting depth discrimination.

We also prefer that the microscope have a drive for fine focusing of the objective or objective turret with which sensors for measuring focus movement are associated. Sending the signals of these sensors to the processor in the evaluation unit allows the object structures being measured to be represented in vertical profile. Microscopes suitable for submicron line-width measuring attachments typically have an electrically actuated focusing drive which acts on the specimen stage and is frequently coupled with an autofocusing device for automatic focusing on the focal plane of the object or structure to be measured. However, we prefer providing a second, highly precise, fine focusing drive for Z-axis movement, serving solely for determining measurement value and operating independently of the microscope table drives. For this purpose, we prefer a flexible element and associated fine focus drive arranged for the objective or the objective turret of the microscope, to provide anti-backlash guidance for the objective. Such a flexible element can advantageously be arranged for supporting the entire upper part of the microscope.

DRAWINGS

DETAILED DESCRIPTION

Figure 1:
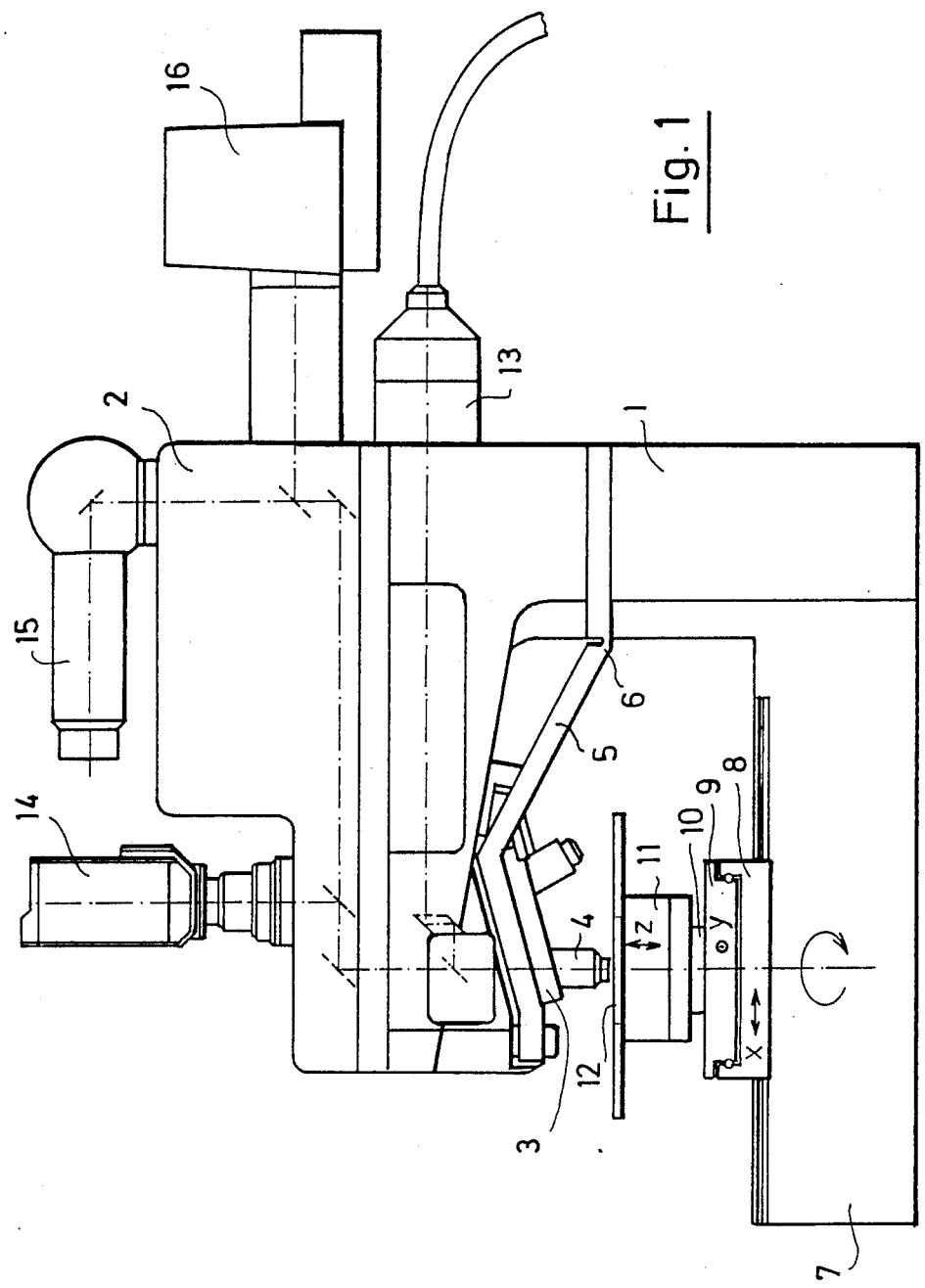
FIG. 1 is a partially schematic, side elevational view of a preferred embodiment of a microscope having a built-in accessory arranged according to our invention for measuring a submicron-sized structure.

The overall device, as shown in FIG. 1, includes a measurement accessory 2 placed on a microscope 1 for the measurement of microscopic structure. A cross slide 8 and 9 displaceable in the X and Y directions is mounted in a base stand 7 of microscope 1. The upper plate 9 of the cross slide has a pivot bearing 10 on which the actual specimen holder 11 is vertically displaceable in the Z direction, for holding a wafer 12 by means of vacuum nozzles (not shown) so that wafer 12 can be measured.

An objective 4, which serves for focusing the surface of wafer 12 on a television camera 14, is mounted on an objective turret 3, which is also vertically adjustable. A flexible plate 5, one end of which is mounted on the microscope stand 1, guides turret 3 in its vertical adjustment. To do this, a notch 6 weakens flexible plate 5 at a pivot point around which flexible plate 5 and objective 4, fastened to plate 5, can pivot. As a result of the movement of flexible plate 5, the optical axis of the microscope theoretically tilts as objective turret 3 moves up and down, but this tilting is so slight, for the total deflection range of only 10 micrometers needed for Z measurement movement of objective 4, that the tilting plays no role in the measurement process. The drive for moving objective 4 in the Z-axis direction has not been shown in FIG. 1, but is explained relative to FIG. 2.

On the rear of microscope stand 1 is a fiber-optical illuminating device 13, which provides incident illumination of wafer 12. The measuring device 2, which is developed as an accessory, has its own source of light in a lamp housing 16, which is also arranged on the rear of microscope 1. A photomultiplier 15, serving as the detector for measurement accessory 2, is mounted at the top, by means of a dovetail.

Figure 4:
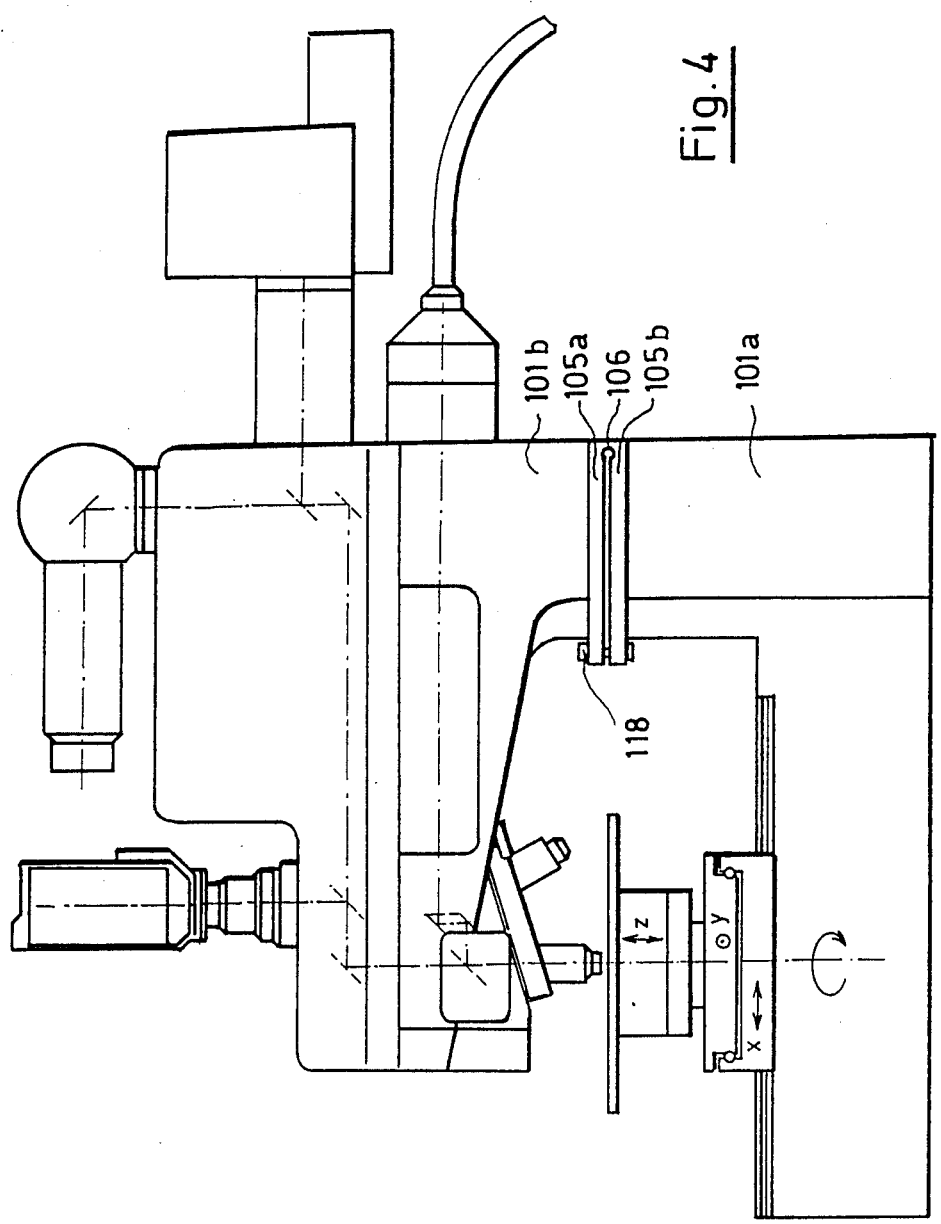
FIG. 4 is a partially schematic, side elevational view, similar to the view of FIG. 1, and showing an alternative preferred embodiment of our invention.

In the alternative preferred embodiment of FIG. 4, the objective turret is not guided separately for Z-axis movement. Instead, the entire upper part 101b of the microscope can be tilted by small angular amounts by means of a flexible plate having the shape of a horizontal U with two horizontal legs, 105a and 105b, fastened respectively to upper microscope part 101b and microscope stand base 101a. A flexure point 106 for the flexible plate is arranged toward the rear of the microscope; and at the front, the two legs 105a and 105b of the flexible plate are connected to each other by a piezodrive 118. In this embodiment, the distance between the microscope objective and the pivot point 106 is very large, to improve the accuracy of Z-axis movement. The relatively large movable mass of the microscope upper part 101b is not important to the measurement process, because of the infrequency of the adjustment movement.

Figure 2:
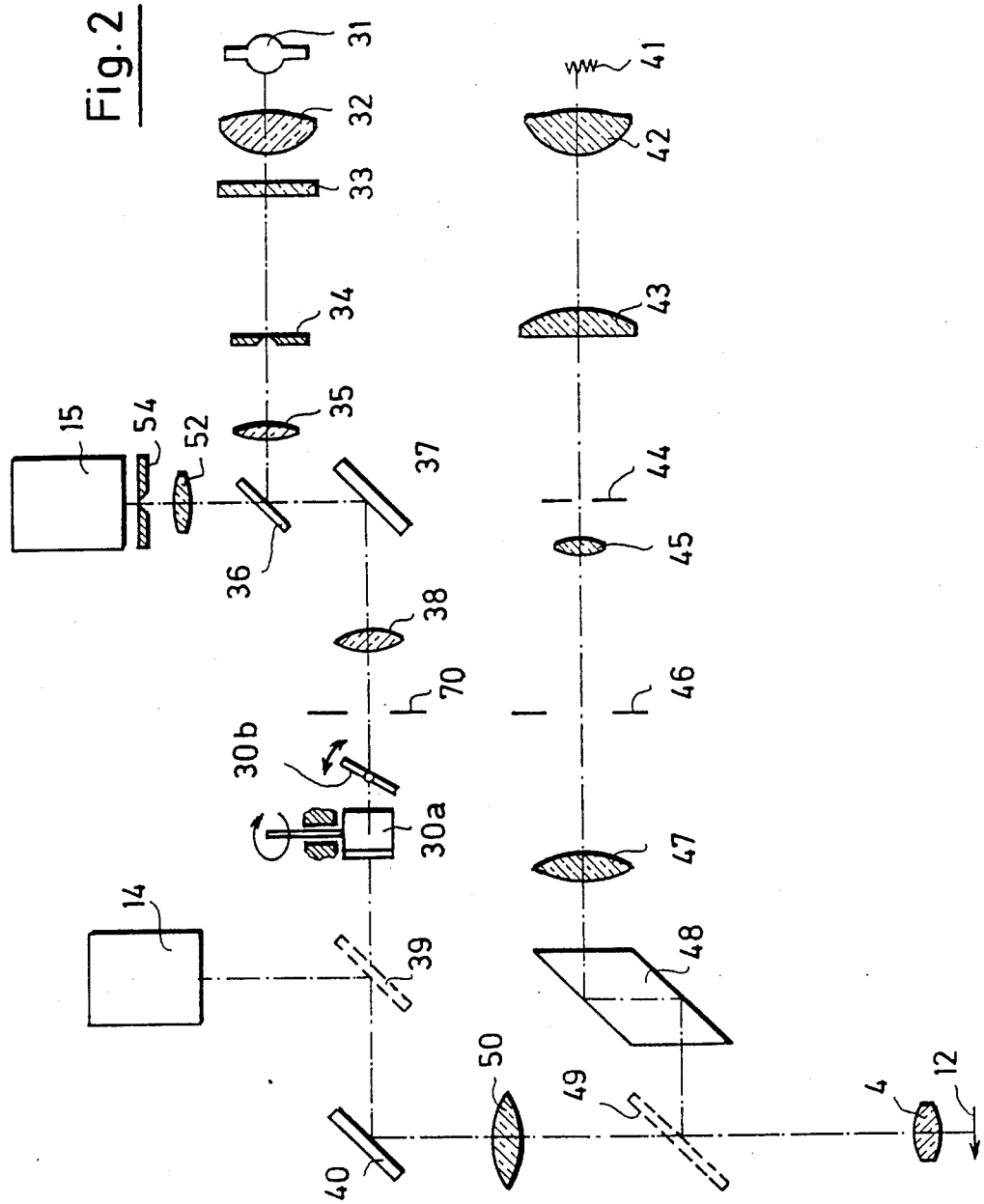
FIG. 2 is a schematic diagram of the optical system preferred for the instrument of FIG. 1.

FIG. 2 schematically shows the optical system of the entire device. The incident light illumination ray path of the microscope comes from a source 41 of light that is focused by a collector 42 and a lens 43 into the plane of an aperture diaphragm 44. Following diaphragm 44, in a generally known manner, is field lens 45 and auxiliary lens 47, which in combination with objective 4 images the field diaphragm 46 in the plane of wafer object 12. Beam splitter 49 mirrors the illumination ray path into the observation ray path of the microscope. Between the beam splitter 49 and the auxiliary lens 47 is a prism step 48, which causes a parallel displacement of the illumination ray path, for adaptation to the mechanical circumstances of the microscope stand.

The observation ray path of the microscope consists of the tube lens 50, a deflection mirror 40, and another beam splitter 39 that deflects the observation ray path toward the video camera 14, which is mounted on top of the microscope. At beam splitter 39, the measurement ray path is reflected into the observation ray path of the microscope.

The illumination unit 16 for the measurement ray path contains an extra high pressure mercury lamp 31 of a standard type. Such a source of light has a very high luminance and a line spectrum, which is superimposed on the continuous spectrum and extends into the UV region. The extra high pressure mercury lamp 31 has a quartz collector 32 arranged in front of it, for focusing light from source 31 on point diaphragm 34. A replaceable interference filter 33 can filter out of the light from source 31 one of the spectral lines (for example, 250 nm or 365 nm). These measures produce a point source of ultraviolet light of high luminance.

The point source of light 34 is focused by two lenses 35 and 38 into the intermediate image plane 70 of the microscope. Between the lenses 35 and 38 is a deflection mirror 37, as well as another beam splitter 36. The beam splitter 36 separates the illumination light in the measurement ray path from the measurement light reflected by the object 12. For detecting this light, the photomultiplier 15 is arranged in the partial ray path which has been mirrored out through a lens 52 and a second point diaphragm 54, which is arranged in a plane conjugate to the point diaphragm 34.

In the non-parallel ray path between the microscope tube lens 50 and the intermediate image plane 70 are two pivotable plane plates 30a and 30b, which can be pivoted around respective axes that are perpendicular to each other. Pivoting motion of plates 30a and 30b moves the measurement spot, which is the image of the point source of light focused via tube lens 50 and objective 4 on the surface of object 12. The optics arranged between the extra high pressure mercury lamp 31 and the object plane 12 in the measurement ray path, including the objective 4 and the tube lens 50, are made of glass that highly transmits UV radiation.

Figure 3:
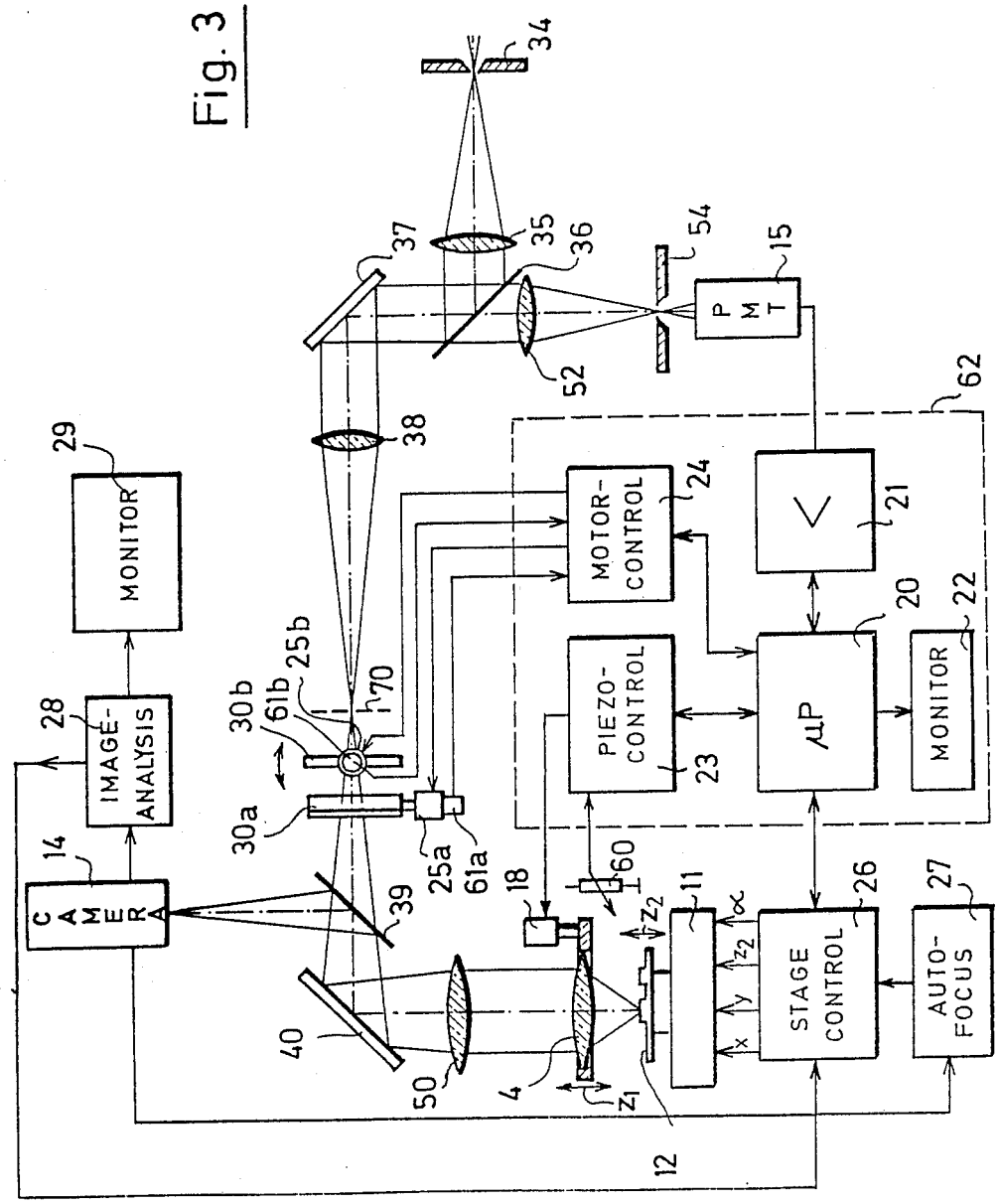
FIG. 3 is a block diagram of a control system associated with the optical system of the instrument of FIG. 1.

For moving the focused light point, for structure width measurement purposes, plane plates 30a and 30b are pivotable through a predetermined range of angular movement. To do this, as shown in FIG. 3, drive motors 25a and 25b are mounted directly on the pivot axes of respective plane plates 30a and 30b, and drive motors 25a and 25b are provided with angle encoders 61a and 61b for reporting the pivot angle of each plate. The actual measurement values are obtained from signals of the encoders 61a and 61b indicating the angular movements of plates 30a and 30b that are used for moving the focused light point over the structure to be measured. Encoders 61a and 61b are therefore connected in the same way as photomultiplier 15 to the evaluation electronics 62 in which the actual measurement value is determined.

The heart of the control or evaluation electronics 62 is a computer or microprocessor 20, which receives the signals of angular movement from the encoders 61a and 61b and is connected to motor control 24, controlling the movement of motors 25a and 25b. Computer 20 indicates to the motor control 24 the amounts by which the two plane plates 30a and 30b are pivoted during a measurement cycle. By corresponding adjustment of the pivot angles of movement of the plane plates 30a and 30b, the measurement spot can be moved in any desired direction in the plane of the object to be measured, which in the illustrated case is the upper surface of wafer 12.

Computer 20 is also connected to the preamplifier 21 of photomultiplier 15. During a measurement cycle, computer 20 stores the intensity of signals of photomultiplier 15, which correspond to positions of the light point moving over the object. At the same time, computer 20 converts pivot angles of plates 30a and 30b, as represented by the signals supplied by the encoders 61a and 61b, into coordinates of the structure being measured on the object 12. This can be done on the basis of known formulas or by a relationship determined in a calibration process.

Computer 20 is also connected to the driver electronics 23 for the piezoelectric drive 18 of the objective turret 3 or objective 4. The measurement spot focused on the object can thus be guided within a range of ±5 micrometers in different focal planes as it passes over the object. The two-dimensional data field resulting from this reproduces the surface profile of wafer 12 with very high precision, and this is shown by computer 20 on the screen of an associated monitor 22. A measurement system 60 reports to computer 20 on the height adjustment caused by piezodrive 18. Since the measurement in the Z-axis direction of the optical axis consists of only small amounts, strain measurement gauges can be used for measurement system 60. Also, piezotranslators with already installed locus sensors are available from the "Physik Instrumente" company (PI) of Karlsruhe under the designation P-172 or P-177 and P841.10 and are suitable for this purpose. In the alternative embodiment shown in FIG. 4, piezodrive 118, driving the entire upper part of the microscope, together with the objective, corresponds to piezodrive 18 and is similarly controlled by controller 23 through a movement that is monitored by measurement system 60.

As already explained relative to FIG. 1, object 12 lies on a table that is movable in all three X, Y, and Z directions and is rotatable about the optical axis. The stage control 26 for the four drives of table 11 also receives its control signals from computer 20. Furthermore, motor control 26 is preferably connected to an autofocusing device 27, which focuses sharply at the start of a measurement cycle by actuating the Z-drive of table 11 until the image of the object shows maximum contrast. For this, autofocusing device 27 evaluates the video signal of camera 14. Of course, some other type of autofocusing device can also be used for this purpose. For instance, the device described in Federal Republic of Germany Patent No. DE 3446727 C2, issued Dec. 4, 1986, by Faltermeier.

An image analyzing device 28 is preferably connected with video camera 14 to effect the positioning and angular orientation of wafer 12. For this, the output of image processing device 28 is connected to stage control 26 for driving table 11. Also, a second monitor 29 on which the image of the surface of wafer 12 appears in the light of the normal incident illumination system 41–48 of the microscope is preferably connected to the image processing device 28.

A typical course of measurements with the above-described instrument goes as follows. After wafer 12 has been placed on table 11, it is positioned in the X and Y directions and in angular orientation with the aid of the image analyzing device 28 so as to identify and properly position the region of the wafer surface selected for measurements. During this movement, the upper surface of wafer 12 is moved along the sharpness plane of the objective 4 by means of the autofocusing device 27. When the object detail to be measured has been set, computer 20 disconnects the Z-drive of table 11 from motor control 26 and carries out the measuring process. This consists of pivoting plane plates 30a and 30b to move the measuring spot, which is the point source of light focused on the wafer surface, so that the spot is guided over the structure to be measured. This is done cyclically; and the position of the focal plane is varied between each cycle by means of the fine drive 18 or 118, for the Z-axis focusing movement of objective 4. Alternatively, it is also possible to drive the cyclic scanning of the object in the Z direction, as carried out primarily via the fine focus drive 18 or 118, and pivot the plane plates 30a and 30b by small amounts between the Z-axis cycles. In both cases, computer 20 associates the maximum intensity of the measurement radiation reflected by the object, as measured by photomultiplier 15, with the corresponding values for the X, Y position of the measurement spot in the focal plane and with the vertical values Z determined by means of the measurement system 60. This produces a three-dimensional profile of the structure being examined.

As already stated, to present the vertical profile in object coordinates requires converting the pivot angles of the plane plates 30a and 30b into actual movement of the measurement spot. The mathematical relationship is essentially a sine function, and the following equation applies:

$$\Delta S = \frac{d}{A} \sin\alpha \left( 1 - \frac{\cos\alpha}{\sqrt{n^2 - \sin^2\alpha}} \right) \quad (1)$$

It contains as parameters the thickness of the plane plate (d), its index of refraction (n), and the magnification (A) of the objective being used.

With current and typical values for parameters, such as $n=1.4$, $d=2$ mm, and $A=100$, then an angle of swing $\alpha$ of 10° gives a shift of the spot $\Delta S$ of about 1 $\mu$m. From this it is clear that with the described system, a resolution of 10 nm and better can easily be obtained, as is desirable for measuring structures in the submicrometer region. Since an angular resolution of a few seconds of angle can be obtained with presently known commercial encoders, without using an interpolator, submicrometer measurement accuracy is assured.

We claim:

1. A microscope arranged for measuring microscopic structures by means of punctiform bundles of rays from a point source of light being focused by an optical system on a structure to be measured so that a photoelectric detector can receive the ray bundles reflected from said structure, said microscope comprising:
   a. a plane plate arranged in a non-parallel ray portion of the path of said optical system, said plate being pivotally mounted for movement through a predetermined angle for moving the focal point of said ray bundles on said structure;
   b. an encoder coupled with said plate for measuring the angle through which said plate is pivoted when moving said focal point; and
   c. a processor, supplied with signals from said encoder corresponding to said angle measurement and with signals from said detector corresponding to the intensity of said reflected ray bundles, for calculating the linear dimensions of said structure over which said focal point has moved.

2. The microscope of claim 1 wherein said light from said point source is ultraviolet and said optical system is adapted for transmitting ultraviolet radiation.

3. The microscope of claim 1 including a point diaphragm arranged in front of said detector in a plane conjugate with a point diaphragm arranged in front of said point source of light.

4. The microscope of claim 1 including a fine focusing drive for an objective of said microscope and wherein focusing drive sensors are arranged for measuring focusing movement of said objective, and signals from said focusing drive sensors are fed to said processor.

5. The microscope of claim 4 including a flexible element providing backlash-free guidance of said objective in the direction of fine focusing movement.

6. The microscope of claim 5 wherein said flexible element is arranged for supporting an upper portion of said microscope.

7. The microscope of claim 4 including an additional focusing drive arranged for electrically adjusting the height of a stage supporting said structure.

8. The microscope of claim 1 including a pair of said plane plates arranged for pivoting on axes perpendicular to each other.

* * * * *